(12) United States Patent
Zones et al.

(10) Patent No.: US 7,750,196 B2
(45) Date of Patent: Jul. 6, 2010

(54) OXYGENATE CONVERSION USING MOLECULAR SIEVE SSZ-75

(75) Inventors: Stacey Zones, San Francisco, CA (US); Allen Burton, Richmond, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 644 days.

(21) Appl. No.: 11/756,820

(22) Filed: Jun. 1, 2007

(65) Prior Publication Data

US 2008/0058571 A1   Mar. 6, 2008

Related U.S. Application Data

(60) Provisional application No. 60/804,259, filed on Jun. 8, 2006.

(51) Int. Cl.
*C07C 1/00* (2006.01)
(52) U.S. Cl. ........................................ 585/640; 585/639
(58) Field of Classification Search .................. 585/639, 585/640
See application file for complete search history.

(56) References Cited

U.S. PATENT DOCUMENTS

| 4,677,242 A | 6/1987 | Kaiser |
| 4,861,938 A | 8/1989 | Lewis et al. |
| 4,910,006 A | 3/1990 | Zones et al. |
| 5,166,111 A | 11/1992 | Zones et al. |
| 5,268,161 A | 12/1993 | Nakagawa |
| 5,316,753 A | 5/1994 | Nakagawa |

OTHER PUBLICATIONS

S. B. Hong, et al., Synthesis, Structure Solution, Characterization, and Catalytic Properties of TNU-10: A High-Silica Zeolite with the STI Topology, Journal of The American Chemical Society, May 12, 2004, Paper No. 10.1021/ja031981t, pp. 5817-5826, vol. 126, Issue 18, American Chemical Society, Washington, D. C.

*Primary Examiner*—In Suk Bullock
(74) *Attorney, Agent, or Firm*—Richard J. Sheridan

(57) ABSTRACT

The present invention relates to new crystalline molecular sieve SSZ-75 having STI framework topology prepared using a tetramethylene-1,4-bis-(N-methylpyrrolidinium) dication as a structure-directing agent and its use in catalysts for converting oxygenates, e.g., methanol, to olefins.

8 Claims, No Drawings

OXYGENATE CONVERSION USING MOLECULAR SIEVE SSZ-75

This application claims benefit under 35 USC 119 of Provisional Application 60/804,259, filed Jun. 8, 2006.

BACKGROUND OF THE INVENTION

1. Field of the Invention

The present invention relates to new crystalline molecular sieve SSZ-75, a method for preparing SSZ-75 using a tetramethylene-1,4-bis-(N-methylpyrrolidinium) dication as a structure directing agent ("SDA") and uses for SSZ-75.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new molecular sieves with desirable properties for gas separation and drying, hydrocarbon and chemical conversions, and other applications. New molecular sieves may contain novel internal pore architectures, providing enhanced selectivities in these processes.

SUMMARY OF THE INVENTION

The present invention is directed to a family of crystalline molecular sieves with unique properties, referred to herein as "molecular sieve SSZ-75" or simply "SSZ-75". SSZ-75 has the framework topology designated "STI" by the IZA. Materials having the STI topology include naturally occurring stilbite and the zeolite designated TNU-10. Stilbite Is disclosed in Breck, Zeolite Molecular Sieves, 1984, Robert E. Krieger Publishing Company where it is reported that stilbite has a typical silica/alumina mole ratio of 5.2. TNU-10 is reported in Hong et al., J. AM. CHEM. SOC. 2004, 126, 5817-5826 as having a silica/alumina mole ratio of about 14. When attempts were made to increase the silica/alumina mole ratio in the product, materials other than TNU-10 were produced.

The present invention relates tea process for the production of light olefins comprising olefins having from 2 to 4 carbon atoms per molecule from an oxygenate feedstock. The process comprises passing the oxygenate feedstock to an oxygenate conversion zone containing a molecular sieve catalyst to produce a light olefin stream.

Thus, in accordance with the present invention there is provided a process for the production of light olefins from a feedstock comprising an oxygenate or mixture of oxygenates, the process comprising reacting the feedstock at effective conditions over a catalyst comprising a crystalline molecular sieve having STI topology and having a mole ratio of at least 15 of (1) an oxide of a first tetravalent element to (2) an oxide of a trivalent element, pentavalent element, second tetravalent element which is different from said first tetravalent element or mixture thereof. The molecular sieve can have a mole ratio of at least 15 of (1) silicon oxide to (2) an oxide selected from aluminum oxide, gallium oxide, iron oxide, boron oxide, titanium oxide, indium oxide and mixtures thereof. The molecular sieve has, after calcination, the X-ray diffraction lines of Table II.

DETAILED DESCRIPTION OF THE INVENTION

The present invention comprises a molecular sieve designated herein "molecular sieve SSZ-75" or simply "SSZ-75".

In preparing SSZ-75, a tetramethylene-1,4-bis-(N-methylpyrrolidinium) dication is used as a structure directing agent ("SDA"), also known as a crystallization template. The SDA useful for making SSZ-75 has the following structure:

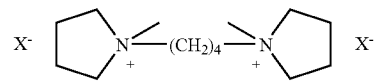

Tetramethylene-1,4-bis-(N-methylpyrrolidinium) dication

The SDA dication is associated with anions ($X^-$) which may be any anion that is not detrimental to the formation of the SSZ-75. Representative anions include halogen, e.g., fluoride, chloride, bromide and iodide, hydroxide, acetate, sulfate, tetrafluoroborate, carboxylate, and the like. Hydroxide is the most preferred anion. The structure directing agent (SDA) may be used to provide hydroxide ion. Thus, it is beneficial to ion exchange, for example, a halide to hydroxide ion.

The tetramethylene-1,4-bis-(N-methylpyrrolidinium) dication SDA can be prepared by a method similar to that described in U.S. Pat. No. 5,166,111, issued Nov. 24, 1992 to Zones et al., which discloses a method for preparing a bis(1,4-diazoniabicyclo[2.2.2]alpha, omega alkane compound, or U.S. Pat. No. 5,268,161, issued Dec. 7, 1993, which discloses a method for preparing 1,3,3,8,8-pentamethyl-3-azoniabicyclo[3.2.1]octane cation. U.S. Pat. No. 5,166,111 and U.S. Pat. No. 5,268,161 are incorporated by reference herein in their entirety.

In general, SSZ-75 is prepared by contacting (1) an active source(s) of silicon oxide, and (2) an active source(s) of aluminum oxide, gallium oxide, iron oxide, boron oxide, titanium oxide, indium oxide and mixtures thereof with the tetramethylene-1,4-bis-(N-methylpyrrolidinium) dication SDA in the presence of fluoride ion.

SSZ-75 is prepared from a reaction mixture comprising, in terms of mole ratios, the following:

TABLE A

| Reaction Mixture | |
| --- | --- |
| $SiO_2/X_aO_b$ | at least 15 (i.e., 15-infinity) |
| $OH^-/SiO_2$ | 0.20-0.80 |
| $Q/SiO_2$ | 0.20-0.80 |
| $M_{2/n}/SiO_2$ | 0-0.04 |
| $H_2O/SiO_2$ | 2-10 |
| $HF/SiO_2$ | 0.20-0.80 | where X is aluminum, gallium, iron, boron, titanium, indium and mixtures thereof, a is 1 or 2, b is 2 when a is 1 (i.e., W is tetravalent); b is 3 when a is 2 (i.e., W is trivalent), M is an alkali metal cation, alkaline earth metal cation or mixtures thereof; n is the valence of M (i.e., 1 or 2); Q is a tetramethylene-1,4-bis-(N-methylpyrrolidinium) dication and F is fluoride.

As noted above, the $SiO_2/X_aO_b$ mole ratio in the reaction mixture is $\geq 15$, This means that the $SiO_2/X_aO_b$ mole ratio can be infinity, i.e., there is no $X_aO_b$ in the reaction mixture. This results in a version of SSZ-75 that is essentially all silica. As used herein, "essentially all silicon oxide" or "essentially all-silica" means that the molecular sieve's crystal structure is comprised of only silicon oxide or is comprised of silicon oxide and only trace amounts of other oxides, such as aluminum oxide, which may be introduced as impurities in the source of silicon oxide.

In practice, SSZ-75 is prepared by a process comprising:

(a) preparing an aqueous solution containing (1) a source(s) of silicon oxide, (2) a source(s) of aluminum oxide, gallium oxide, iron oxide, boron oxide, titanium oxide, indium oxide and mixtures thereof, (3) a source of fluoride ion and (4) a tetramethylene-1,4-bis-(N-methylpyrrolidinium) dication having an anionic counterion which is not detrimental to the formation of SSZ-75;

(b) maintaining the aqueous solution under conditions sufficient to form crystals of SSZ-75; and (c) recovering the crystals of SSZ-75.

The reaction mixture is maintained at an elevated temperature until the crystals of the SSZ-75 are formed. The hydrothermal crystallization is usually conducted under autogenous pressure, at a temperature between 100° C. and 200° C., preferably between 135° C. and 180° C. The crystallization period is typically greater than 1 day and preferably from about 3 days to about 20 days. The molecular sieve may be prepared using mild stirring or agitation.

During the hydrothermal crystallization step, the SSZ-75 crystals can be allowed to nucleate spontaneously from the reaction mixture. The use of SSZ-75 crystals as seed material can be advantageous In decreasing the time necessary for complete crystallization to occur. In addition, seeding can lead to an increased purity of the product obtained by promoting the nucleation and/or formation of SSZ-75 over any undesired phases. When used as seeds, SSZ-75 crystals are added in an amount between 0.1 and 10% of the weight of the first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-75 crystals. The drying step can be performed at atmospheric pressure or under vacuum.

SSZ-75 as prepared has the X-ray diffraction lines of Table I below. SSZ-75 has a composition, as synthesized (i.e., prior to removal of the SDA from the SSZ-75) and in the anhydrous state, comprising the following (in terms of mole ratios):

| | |
|---|---|
| $SiO_2/X_cO_d$ | at least 15 (i.e., 15-infinity) |
| $M_{2/n}/SiO_2$ | 0-0.03 |
| $Q/SiO_2$ | 0.02-0.08 |
| $F/SiO_2$ | 0.01-0.04 | wherein X is aluminum, gallium, iron, boron, titanium, indium and mixtures thereof, c is 1 or 2; d is 2 when c is 1 (i.e., W is tetravalent) or d is 3 or 5 when c is 2 (i.e., d is 3 when W is trivalent or 5 when W is pentavalent), M is an alkali metal cation, alkaline earth metal cation or mixtures thereof; n is the valence of M (i.e., 1 or 2); Q is a tetramethylene-1,4-bis-(N-methyl-pyrrolidinium) dication and F is fluoride.

SSZ-75 (whether in the as synthesized or calcined version) has a $SiO_2/X_cO_d$ mole ratio of at least 15 (i.e., 15-infinity), for example 20-infinity or 40-infinity.

SSZ-75 has the STI framework topology. It is characterized by its X-ray diffraction pattern. SSZ-75, as-synthesized, has a crystalline structure whose X-ray powder diffraction pattern exhibits the characteristic lines shown in Table I.

TABLE I

As-Synthesized SSZ-75

| 2 Theta | d-spacing (Angstroms) | Relative Integrated Intensity (%) |
|---|---|---|
| 10.04 | 8.80 | VS |
| 17.17 | 5.16 | W |
| 19.44 | 4.56 | S |
| 21.13 | 4.20 | W-M |
| 22.36 | 3.97 | VS |
| 22.49 | 3.95 | M |
| 24.19 | 3.68 | W |
| 26.61 | 3.35 | W |
| 28.49 | 3.13 | W |
| 30.20 | 2.96 | M |

(a) ±0.1
(b) The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized SSZ-75 including actual relative intensities.

TABLE IA

As-Synthesized SSZ-75

| 2 Theta | d-spacing (Angstroms) | Relative Integrated Intensity (%) |
|---|---|---|
| 9.84 | 8.98 | 7 |
| 10.04 | 8.80 | 100 |
| 13.24 | 6.68 | 7 |
| 14.19 | 6.24 | 4 |
| 17.17 | 5.16 | 13 |
| 19.44 | 4.56 | 47 |
| 20.01 | 4.43 | 2 |
| 20.17 | 4.40 | 7 |
| 21.13 | 4.20 | 21 |
| 22.36 | 3.97 | 84 |
| 22.49 | 3.95 | 38 |
| 24.19 | 3.68 | 12 |
| 26.13 | 3.41 | 7 |
| 26.61 | 3.35 | 17 |
| 28.49 | 3.13 | 18 |
| 29.31 | 3.04 | 10 |
| 30.20 | 2.96 | 30 |
| 30.30 | 2.95 | 7 |
| 31.94 | 2.80 | 2 |
| 32.12 | 2.78 | 1 |
| 32.61 | 2.74 | 3 |
| 33.13 | 2.70 | 4 |
| 33.59 | 2.67 | 6 |
| 34.86 | 2.57 | 7 |
| 35.13 | 2.55 | 5 |
| 35.75 | 2.51 | 6 |
| 36.55 | 2.46 | 2 |
| 36.69 | 2.45 | 1 |
| 37.19 | 2.42 | 1 |

(a) ±0.1

After calcination, the X-ray powder diffraction pattern for SSZ-75 exhibits the characteristic lines shown in Table II below.

TABLE II

Calcined SSZ-75

| 2 Theta | d-spacing (Angstroms) | Relative Integrated Intensity (%) |
|---|---|---|
| 9.64 | 9.17 | W |
| 9.95 | 8.88 | VS |

TABLE II-continued

Calcined SSZ-75

| 2 Theta | d-spacing (Angstroms) | Relative Integrated Intensity (%) |
|---|---|---|
| 10.06 | 8.79 | M |
| 13.14 | 6.73 | W |
| 19.38 | 4.58 | W |
| 21.03 | 4.22 | W |
| 22.35 | 3.97 | M-S |
| 24.19 | 3.68 | W |
| 28.37 | 3.14 | W |
| 30.16 | 2.96 | W |

(a) ±0.1

Table IIA below shows the X-ray powder diffraction lines for calcined SSZ-75 including actual relative intensifies.

TABLE IIA

Calcined SSZ-75

| 2 Theta | d-spacing (Angstroms) | Relative Integrated Intensity (%) |
|---|---|---|
| 9.64 | 9.17 | 8 |
| 9.95 | 8.88 | 100 |
| 10.06 | 8.79 | 24 |
| 13.14 | 6.73 | 7 |
| 14.17 | 6.25 | 2 |
| 17.13 | 5.17 | 2 |
| 17.25 | 6.14 | 3 |
| 19.38 | 4.58 | 15 |
| 20.23 | 4.39 | 1 |
| 21.03 | 4.22 | 10 |
| 22.35 | 3.97 | 39 |
| 22.54 | 3.94 | 6 |
| 24.19 | 3.68 | 7 |
| 25.24 | 3.53 | 6 |
| 26.08 | 3.41 | 2 |
| 26.48 | 3.36 | 6 |
| 28.37 | 3.14 | 7 |
| 29.25 | 3.05 | 3 |
| 30.16 | 2.96 | 13 |
| 30.32 | 2.95 | 2 |
| 32.18 | 2.78 | 1 |
| 33.02 | 2.71 | 2 |
| 33.54 | 2.67 | 2 |
| 34.57 | 2.59 | 1 |
| 34.94 | 2.57 | 2 |
| 35.09 | 2.56 | 1 |
| 35.68 | 2.51 | 2 |
| 36.58 | 2.45 | 1 |
| 37.07 | 2.42 | 1 |

(a) ±0.1

The X-ray powder diffraction patterns were determined by standard techniques. The radiation was CuKalpha radiation. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.1 degrees.

Representative peaks from the X-ray diffraction pattern of as-synthesized SSZ-75 are shown in Table I. Calcination can result in changes in the intensities of the peaks as compared to patterns of the "as-synthesized" material, as well as minor shifts in the diffraction pattern.

Crystalline SSZ-75 can be used as-synthesized, but preferably will be thermally treated (calcined). Usually, it is desirable to remove the alkali metal cation (if any) by ion exchange and replace it with hydrogen, ammonium, or any desired metal ion. Calcined SSZ-75 has an n-hexane adsorption capacity of about 0.15 cc/g.

SSZ-75 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen, in cases where the catalyst is molded, such as by extrusion with an organic binder, the SSZ-75 can be extruded before drying, or, dried or partially dried and then extruded.

SSZ-75 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

SSZ-75 is useful as an adsorbent for gas separations (owing to its high pore volume while maintaining diffusion control and hydrophobicity). SSZ-75 can also be used in a catalyst for converting oxygenates (such as methanol) to olefins, and for making small amines. SSZ-75 can be used to reduce oxides of nitrogen in gas streams (such as automotive exhaust), SSZ-75 can also be used as a cold start hydrocarbon trap in combustion engine pollution control systems, SSZ-75 is particularly useful for trapping $C_3$ fragments.

The present invention comprises a process for catalytic conversion of a feedstock comprising one or more oxygenates comprising alcohols and ethers to a hydrocarbon product containing light olefins, i.e., $C_2$, $C_3$ and/or $C_4$ olefins. The feedstock is contacted with the molecular sieve of the present invention at effective process conditions to produce light olefins.

The term "oxygenate" as used herein designates compounds such as alcohols, ethers and mixtures thereof. Examples of oxygenates include, but are not limited to, methanol and dimethyl ether.

The process of the present invention may be conducted in the presence of one or more diluents which may be present in the oxygenate feed in an amount between about 1 and about 99 molar percent, based on the total number of moles of all feed and diluent components. Diluents include, but are not limited to, helium, argon, nitrogen, carbon monoxide, carbon dioxide, hydrogen, water, paraffins, hydrocarbons (such as methane and the like), aromatic compounds, or mixtures thereof, U.S. Pat. Nos. 4,881,938 and 4,677,242, which are incorporated by reference herein in their entirety, emphasize the use of a diluent to maintain catalyst selectivity toward the production of light olefins, particularly ethylene.

The oxygenate conversion is preferably conducted in the vapor phase such that the oxygenate feedstock is contacted in a vapor phase in a reaction zone with the molecular sieve of this invention at effective process conditions to produce hydrocarbons, i.e., an effective temperature, pressure, weight hourly space velocity (WHSV) and, optionally, an effective amount of diluent. The process is conducted for a period of time sufficient to produce the desired light olefins. In general, the residence time employed to produce the desired product can vary from seconds to a number of hours. It will be readily appreciated that the residence time will be determined to a significant extent by the reaction temperature, the molecular sieve catalyst, the WHSV, the phase (liquid or vapor) and process design characteristics. The oxygenate feedstock flow rate affects olefin production. Increasing the feedstock flow rate increases WHSV and enhances the formation of olefin production relative to paraffin production. However, the enhanced olefin production relative to paraffin production is offset by a diminished conversion of oxygenate to hydrocarbons.

The oxygenate conversion process is effectively carried out over a wide range of pressures, including autogenous pressures. At pressures between about 0.01 atmospheres (0.1 kPa) and about 1000 atmospheres (101.3 kPa), the formation of light olefins will be affected although the optimum amount of product will not necessarily be formed at all pressures. The preferred pressure is between about 0.01 atmospheres (0.1 kPa) and about 100 atmospheres (10.13 kPa). More preferably, the pressure will range from about 1 to about 10 atmospheres (101.3 kPa to 1.013 Mpa). The pressures referred to herein are exclusive of the diluent, if any, that is present and refer to the partial pressure of the feedstock as it relates to oxygenate compounds.

The temperature which may be employed in the oxygenate conversion process may vary over a wide range depending, at least in part, on the molecular sieve catalyst. In general, the process can be conducted at an effective temperature between about 200° C. and about 700° C. At the lower end of the temperature range, and thus generally at a lower rate of reaction, the formation of the desired light olefins may become low. At the upper end of the range, the process may not form an optimum amount of light olefins and catalyst deactivation may be rapid.

The molecular sieve catalyst preferably is incorporated into solid particles in which the catalyst is present in an amount effective to promote the desired conversion of oxygenates to light olefins. In one aspect, the solid particles comprise a catalytically effective amount of the catalyst and at least one matrix material selected from the group consisting of binder materials, filler materials and mixtures thereof to provide a desired property or properties, e.g., desired catalyst dilution, mechanical strength and the like to the solid particles. Such matrix materials are often, to some extent, porous in nature and may or may not be effective to promote the desired reaction. Filler and binder materials include, for example, synthetic and naturally occurring substances such as metal oxides, clays, silicas, aluminas, silica-aluminas, silica-magnesias, silica-zirconias, silica-thorias and the like. If matrix materials are included in the catalyst composition, the molecular sieve preferably comprises about 1 to 99%, more preferably about 5 to 90%, and still more preferably about 10 to 80% by weight of the total composition.

EXAMPLES

The following examples demonstrate but do not limit the present invention.

Example 1

Synthesis of Al-Containing SSZ-75

1.5 mM of tetramethylene-1,4-bis-(N-methylpyrrolidinium) dication SDA (3 mM OH⁻) was mixed in a Teflon cup (for a Parr 23 ml reactor) with 1.26 grams of tetraethylorthosilicate and the cup was placed in a hood to evaporate (as ethanol is formed from hydrolysis) over several days. When all of the visible liquid was gone, the Teflon cup was reweighed and water was added to bring the $H_2O/SiO_2$ mole ratio to about four. Then, 12 mg of Reheiss F2000 (50% $Al_2O_3$) was added and dissolved into the reaction mixture. This represents a starting synthesis mole ratio of $SiO_2/Al_2O_3$ of 100. Lastly, 0.135 gram of 50% HF was added using a plastic pipette. The gel was mixed with a plastic spatula and then the resulting reaction mixture was heated in a closed vessel rotating at 43 RPM at 150° C. for 16 days. A crystalline product formed which was recovered and found by X-ray diffraction analysis to be molecular sieve SSZ-75.

Example 2

Synthesis of Al-Containing SSZ-75

The procedure described in Example 1 was repeated, except that the source of aluminum was LZ-210 zeolite (a form of dealuminated FAU) and the $SiO_2/Al_2O_3$ mole ratio was 70. The reaction formed SSZ-75 in 10 days.

Example 3

Synthesis of Al-Containing SSZ-75

The procedure described in Example 1 was repeated, except that the source of aluminum was Catapal B (a form of pseudoboehmite alumina). The reaction formed SSZ-75 in 10 days.

Examples 4-7

Synthesis of All-Silica SSZ-75

A procedure similar to that of Example 1 was repeated using the reaction mixture (expressed as mole ratios) and conditions shown in the table below. The reactions were run until a crystalline product was observed by SEM, and then the product was recovered. The products are also shown in the table.

| Ex. | SDA/$SiO_2$ | $NH_4F/SiO_2$ | $HF/SiO_2$ | $H_2O/SiO_2$ | ° C./RPM | Prod. |
|---|---|---|---|---|---|---|
| 4 | 0.50 | 0.0 | 0.50 | 5.0 | 150/43 | SSZ-75 |
| 5 | 0.40 | 0.1 | 0.40 | 5.0 | 150/43 | SSZ-75 |
| 6 | 0.30 | 0.2 | 0.30 | 5.0 | 150/43 | MTW |
| 7 | 0.20 | 0.3 | 0.20 | 5.0 | 150/43 | Amor. ZSM-48 |

Example 8

Calcination of SSZ-75

The product from Example 1 was calcined in the following manner. A thin bed of material was heated in a flowing bed of air in a muffle furnace from room temperature to 120° C. at a rate of 1° C. per minute and held at 120° C. for two hours. The temperature is then ramped up to 540° C. at the same rate and held at this temperature for three hours, after which it was increased to 594° C. and held there for another three hours.

Example 9

Conversion of Methanol

The calcined material of Example 8 (0.10) gram) was pelleted and meshed (with recycling) to 20-40 mesh and packed into a ⅜ inch stainless steel reactor. After sufficient purge with nitrogen carrier gas (20 cc/min), the catalyst was heated to 750° F. (399° C.). A feed of 22.5% methanol in water was introduced into the reactor via syringe pump at a rate of 1.59 cc/hr. A sample of the effluent stream was diverted to an on-line gas chromatograph at ten minute point of feed introduction. SSZ-75 showed the following behavior:

Methanol conversion=100%
No dimethylether detected
$C_2$-$C_4$ is about 70% of the product
$C_{5+}$ showed a mixture of olefins and saturates Aromatics were made with ethylbenzene the most abundant single product Trimethylbenzene isomers were observed as the heaviest products At 100 minutes on stream the SSZ-75 was fouling, but still produced the same products (although very few aromatics were observed).

What is claimed is:

1. A process for the production of light olefins from a feedstock comprising an oxygenate or mixture of oxygenates, the process comprising reacting the feedstock at effective conditions over a catalyst comprising a crystalline molecular sieve having STI topology and having a mole ratio of at least 15 of (1) an oxide of a first tetravalent element to (2) an oxide of a trivalent element, pentavalent element, second tetravalent element which is different from said first tetravalent element or mixture thereof.

2. The process of claim 1 wherein the molecular sieve has a mole ratio of at least 15 of (1) silicon oxide to (2) an oxide selected from aluminum oxide, gallium oxide, iron oxide, boron oxide, titanium oxide, indium oxide and mixtures thereof.

3. The process of claim 1 wherein the molecular sieve has, after calcination, the X-ray diffraction lines of Table II.

4. The process of claim 2 wherein the molecular sieve has, after calcination, the X-ray diffraction lines of Table II.

5. The process of claim 2 wherein the light olefins are ethylene, propylene, butylene or mixtures thereof.

6. The process of claim 5 wherein the light olefin is ethylene.

7. The process of claim 2 wherein the oxygenate is methanol, dimethyl ether or a mixture thereof.

8. The process of claim 7 wherein the oxygenate is methanol.

* * * * *